United States Patent [19]

Pierpaoli et al.

[11] Patent Number: 4,746,674

[45] Date of Patent: May 24, 1988

[54] MELATONIN COMPOSITIONS AND USES THEREOF

[75] Inventors: Walter Pierpaoli, Ebmatingen, Switzerland; William Regelson, Richmond, Va.

[73] Assignee: Cellena (Cell Engineering) AG, Zurich, Switzerland

[21] Appl. No.: 770,054

[22] Filed: Aug. 27, 1985

[51] Int. Cl.$^4$ ................... A61K 31/40; A61K 31/405
[52] U.S. Cl. ................... 514/415; 514/419; 514/859; 514/864
[58] Field of Search ................ 514/415, 419

[56] References Cited

U.S. PATENT DOCUMENTS 4,161,525 7/1979 Voorhees ............... 514/415

OTHER PUBLICATIONS

Rose et al, J. of Animal Science, vol. 58, No. 1, 57-61 (1984).
Gimeno et al, Inhibition by Melatonin of Prostaglandin Synthesis, 147-151.
Reiter et al, Reproductive Consequences of Melatonin in Mammals, 151-157.
J. of Invest. Derm, 79:275-278 (1982).
Birau, Melatonin in Human Serum: Process in Screening, Invest. and Clinic, 297-326.
Heath & Lynch, General and Comparative Endocrinology, 48, 289-295 (1982).
Houssay et al, Acta Physiologica Latino Americana, vol. XVI, 202-207 (1966).
Houssay et al, J. of Invest. Derm., vol. 47, No. 3, 220-234 (1966).
Starr, Progress in Clinical Cancer, vol. IV, Grune & Stratton, 1, 3, 9, 12, 13, 18-20 & 22-27.
Pigatto et al, Arch. Derm. Res. 277: 185-189 (1985).
Birau et al, Melatonin: Current Status & Perspectives, Permagon Press, 297, 307-308.
Edelson et al, Scientific American, 46-53 (1985).
Kauer et al, Indian Heart Journal, vol. 35, No. 3 (1983).
Logan et al, J. Invest. Derm., vol. 74, No. 1, 47-50 (1980).
Manewski et al, Arch. Derm. Res., 277: 77-78 (1978).
Schloot et al, Genetics of Melatonin.
Chemical Abstracts 67: 31373m, 1967, (Barchas et al).

*Primary Examiner*—Leonard Schenkman
*Attorney, Agent, or Firm*—Weiser and Stapler

[57] ABSTRACT

A method for treating the skin and/or scalp of a human host by the administration of a melatonin composition in order to improve the cosmetic or physical appearance of the skin and/or scalp, and the compositions therefore.

19 Claims, No Drawings

MELATONIN COMPOSITIONS AND USES THEREOF

FIELD OF THE INVENTION

The present invention primarily relates to a method and composition for topically treating the skin and/or scalp of a human host. More particularly, the present invention relates to the topical treatment of specific conditions of the skin and scalp of a human host so as to enhance the condition of the skin and to treat areas of hair growth either to selectively remove hair from areas which normally do not have hair growth or to assist in the rejuvenation of partially degenerated hair follicles by using melatonin compounds.

Even more particularly, the present invention relates to a method and composition for enhancing skin condition and tone, the prevention or amelioration of the conditions or symptoms of acne, seborrhea, hirsuitism and for the rejuvenation of partially degenerated hair follicles through the use of malatonin compounds, homologues or derivatives.

BACKGROUND OF THE INVENTION

Melatonin is a hormone secreted by the pineal gland that controls seasonal and circadian hormonal rhythms, and alters the metabolism of testosterone and enhances the availability of estrogen receptors in target tissues.

Since the isolation of melatonin in 1959, reports of its ability to inhibit luteinizing hormone (LH) secretion with control of fertility led researchers (Flaugh et al., 1978) to investigate the action of melatonin analogs on plasma half life to produce compounds with the same biological activity as malatonin but with a prolonged serum half-life.

Schloot et al have determined that patients suffering from psoriasis have a severe disorder of melatonin secretion. Treatment with psoralen for rising the serum melatonin concentration of the patient is suggested. They suggested that the antimitotic effect of melatonin may be of importance for the regulation of increased epidermal mitotic rate and decreased cell turnover time.

Houssay et al (1966) (1) have shown that the pineal gland and the parenteral administration of melatonin acts on the skin of mice to slow hair growth waves in mice.

Houssay et al (1966) (2) describe that the parenteral treatment of mice with melatonin effects the hair growth waves in mice.

Rose et al (1984) have shown that it is possible to induce the growth of winter pelage in mink by implanting melatonin.

Logan et al (1980) have found that melatonin can inhibit in vitro melanogenesis in hair follicles of the Siberian hamster.

Heath et al (1982) have shown that follicular development was blocked in mice injected with melantonin.

Rats were used in the assay to measure effects on LH release and ovulation. Melatonin analogs were given p.o. and intravenously. Pronounced increase in activity and half-life was noted with halogenation on the 6 position.

Frohn et al (1980) reported a structural activity relationships between 23 indoleamines and melatonin utilizing an in vitro fish pigment bioassay. Indoles were dissolved in ethanol and given intraperitoneally. In this model, halogenation a 6- position and minor variations of the N-acyl group were without effect on comparable in vivo activity. Indole was found to be more active than melatonin. The 6-chloro-2,3-dihydromelatonin was believed to be a possible long acting melatonin agonist.

In a study of antagonists to the brain receptors for diazepam, melatonin and metabolites were tested to determine the inhibition of diazepam binding to rat synaptosomal membranes. Melatonin and its CNS metabolite N-acetyl 5-methoxy kynurenamine were found to be the most potent antagonists and beta carboline metabolites of melatonin were also noted as high affinity antagonists to diazepam (Marangos et al., 1981).

Rollag (1982) studied 18 different tryptophan derivatives, many of which are found in the pineal gland, to induce gonodal regression and aspermia in syrian hamsters. Only melatonin and 5-methoxy tryptamine were found to possess anti-gonadotrophin action. The action of 5-methoxytryptamine is supported in Pevet's review (1983) but melatonin is the most effective agent.

Similar studies were conducted by Richardson et al (1983), Vaughn et al (1983) with 6-chloromelatonin being the only analogue to possess anti-gonadotrophic activity equal to melatonin. Their paper reviews the structural activity literature evaluating melatonin analogues. This same group (Vaughan et al., 1982) explored the action of melatonin natural and synthetic analogues on the effects of cholesterol and thyroid levels in the male syrian hamsters as compared to melatonin. The native hormone melatonin was found to be the only structure lowering $T_4$ (thyroxine) levels.

In a frog skin assay, Frohn, et al., (1980) concluded that the N-acetyl group attached to 3- position determines binding site affinity while the 5-methoxy group confers activity.

Melatonin and related metabolites were found to be the principal excretory products of the pineal gland (epiphysis cereberi), an endocrine organ present intracranially in all vertebrates (Reiter, 1983). In lower vertebrates there are true morphological photoreceptors present in the pineal gland but in mammals the pineal gland receives signals from neural sympathetic sources which effect the production of its principal secretory product melatonin (Reiter, 1983). The primary secretory route of melatonin in mammals is by way of the capillary bed of the gland itself (Rollag et al, 1977).

Melatonin (N-acetyl-methoxytryptamine) is primarily derived from tryptophan and synthesized via the action of tryptophane hydroxylase (Lovenberg et al., 1967). The pineal gland is the primary place for a major portion of physiological indolamine metabolism including that of the neuroeffector serotonin which is a major source of melatonin synthesis.

Melatonin synhesis is governed by light exposure and in man and other mammals and primarily produced in conjunction with night or in darkness from its pineal endocrine source. In addition to the pineal body, both the retina, the harderian gland (in rodents) and gastrointestinal tract are producers of melatonin (Ralph, 1981; Reiter et al, 1983: Raikhlin et al., 1975).

Besides melatonin, 5-methoxytopol (Wilson et al., 1978) and 5-methoxytryptamine (Pevet et al., 1983) are produced by the pineal and have been found to have endocrine effects.

The primary role of the pineal gland relates to its control of reproductive physiology (Tamarkin et al., 1985; Arendt et al., 1983; Stetson & Watson-Whitmyre, 1984). As mentioned previously, secretion of melatonin is governed by light to dark exposure of the animal and there are short day or long day seasonal breeding animals who are influenced differently by melatonin production governed by the seasonal light cycle.

An example of systemic melatonin effects on reproductive hormonal cycling are seen in the depression of testosterone production in mice given melatonin (Petterborg and Reiter, 1981). Alternatively, depending on species, testicular regression can be prevented and testosterone activity maintained (Turek, 1977; Stetson et al 1983) in hamsters. Melatonin, given by injection, can alter estrous cycling in female rats (Trentini, et al., 1980). Evidence supports the possibility that melatonin levels may be a factor in suppression of puberty in man (Tamarkin et al., 1985).

Melatonin is entering the commercial animal husbandry market to control fertility (breeding time), fur coat development and appetite. For example in ewes 2 mg/day, in pelleted feed, which mimics nocturnal blood levels, controls the estrous cycle and sheep fertility (Lincoln, 1983); (Kennaway et al., 1982). Similar effects on daily feeding have been observed in male white tailed deer (Bubenik, 1983) with earlier seasonal antler and coat changes.

Melatonin injected subcutaneously in saline or oil produces high transient blood levels while oral administration in saline or food pellets produces sustained blood levels (Kennaway and Seamark, 1980). Melatonin has been orally given in drinking water (Pevet and Haldar-Misra, 1982) or by subcutaneous slow release implants, i.e., sialastic (Turek, 1977; Losee and Turek, 1980; Kennaway and Gilmore, 1984) or by injection (Sisk and Turek, 1982).

The duration of melatonin exposure is significant since constant levels can produce refractoriness, thus intermittant exposure and the relation of melatonin to the animals photoperiod (light/dark cycle) is important (Stetson et al., 1983; Losee and Turek, 1980; Trentini et al., 1980; Stetson and Tay, 1983; Bittman, 1984; Tamarkin et al., 1985).

Melatonin injections can mimic syrian hamster short day photoperiod exposure with increases in body weight gain, feed efficiency, enhanced carcass lipid and brown adipose tissue mass and thermogenic capacity (Bartness and Wade, 1984).

The clinical use of melatonin in CNS disease has been reviewed by Anton-Tay (1974) and Romijn (1978) and there have been extensive studies of its intravenous, intrathecal and direct localized CNS implantation on behavior in a wide range of animal species that has led to clinical trial.

Waldhauser et al. (1984) have reviewed the clinical use of melatonin. They indicate that approxiamtely 150 subjects have received clinical melatonin intravenously or orally. In most cases, no significant toxicity was observed (Lerner and Norlund, 1978). As much as 3-6 gms of maltonin has been given orally daily for 1 month with reports of abdominal cramping and tranquilization (Papavasiliou, et al., 1972).

Melatonin has been given clinically to volunteers by mouth in carbowax at 1-25 ug/kg (Anton-Tay, 1974) or clinically to volunteers by mouth in corn oil as a 0.04% solution at a dose of 2 mg/day for 4 weeks (Arendt et al, 1984). It has been given orally in doses of 250 mg (Norlund and Lerner, 1977) and in doses up to 1.2 g/day (Anton-Tay, 1974; Carmen et al., 1976; Anton-Tay et al., 1971). These studies have demonstrated a systemic effect of melatonin with reports of melatonin induced fatigue and depression or sleep.

Melatonin has been given to human subjects in doses of 50 mg intravenously (Pavel et al., 1981; Cramer et al., 1974) where it induced sleep with normal or enhanced REM electroencephalographic patterns. Melatonin's sedative action has been confirmed by H. Lieverman, as cited by Walkhauser et al (1984), and are supported by the results of intranasal administration where melatonin, as a 0.85 percent ethanol spray induced sleep in 70 percent of patients within 40-60 minutes (Vollrath et al., 1981).

Melatonin has been studied p.o. and i.v. clinically in depression and in Huntington's chorea with no improvement or clinical worsening (Carman et al., 1976). In two patients with schizophrenia, I.V. melatonin (300 mg) worsened hallucinatory symptoms (Altschule cited by Carman et al., 1976).

In epilepsy, melatonin has produced some benefit on i.v. administration at a 1 percent solution in ethanol at dosages up to 1.25 mg/kg i.e. In Parkinsonism, given i.v. or p.o. for a daily total of 1.2 gms for 4 weeks (Anton-Tay et al., 1971), amelioration of tremor and rigidity have been seen although results have not been consistent in studies of Parkinsonism with all investigators as Papavasilou et al., 1972 has not seen benefit with doses as high as 6 gms daily. Carman et al. (1976) have reviewed the CNS clinical studies up to that time and the use of melatonin for the treatment of tremor and rigidity looked promising.

Melatonin has been given at dosages of 1 mg/kg i.m. with advanced breast cancer for periods up to 2 months. These studies were conducted after trial at 5 and 20 mg/kg i.m. daily for up to 10 days in monkeys with no report on clinical response other than a report of a decline in urinary estrogen (Burns, 1973). Blask (1984) has reviewed the role of melatonin in the clinical treatment of malignancy. He cites DiBella and Starr as achieving inhibitory clinical results in a variety of tumors.

In relation to endocrine action, Symthe and Lazarus (1974) have given 0.5 gms of melatonin for 2 doses, 30 minutes apart with a reported melatonin related rise in growth hormone.

Melatonin has been used in veterinary medicine in the treatment of acanthosis nigricans in dogs. This disease is associated with thickening of the skin, pigmentation and pruritus. Rickards (1965) and Kirk (1979) have successfully treated canine acanthosis nigricans by subcutaneous injection utilizing 2 mg injections of melatonin for daily and extended weekly treatment periods.

In regard to local modulation and inhibition of steroid synthesis, melatonin on in vivo and in vitro treatment has shown in vivo and in vitro inhibition of testicular synthesis from cholesterol and pregnenolone precursors of testosterone and androstenedione synthesis in the rat testes (Peat and Kinson, 1971).

The inhibiting effects of melatonin on testicular function have been associated with stimulation of delta-4-reductase in rat liver and hypothalamus (Frehn et al., 1974). Melatonin was found to specifically increase the 5-alpha reductase of seminiferous tubules for both progesterone and testosterone. Melatonin decreased androgen synthesis in both testicular interstitial cells and tubules (Ellis, 1972). Similar increases in 5 alpha reductase activity in rats by melatonin have been observed on adrenal cortical function (Ogle and Kitay, 1977).

Melatonin reduced accessory sexual organ size in pinealectomized male rats kept in constant darkness without inhibiting testosterone metabolism leading the authors (Shirama et al., 1982) to suggest that melatonin is possibly acting at the tissue level to reduce the number of androgen receptors and/or the susceptability to androgen.

Orally administered, melatonin was found to lower ventral prostate and seminal vesicle weight and the 3/beta-hydroxysteroid oxidoreductase was increased but not the 5 alpha reductase in the ventral prostate and seminal vesicles of pinealectomized rats (Horst et al., 1982). The authors felt that this reflects on increased androgenic catabolism resulting in prostatic involution. The effects of melatonin on prostatic androgen receptors can depend on the age of the animal and light cycle exposure (Moeller et al., 1983).

Melatonin in vitro when combined with chorinonic gonadotrophin or ovine luteinizing hormone increased the secretion of estrogens and progesterone in isolated granulosa cells of the rat. Melatonin, in relation to ovarian function, showed a progonadal trophic effect (Fiske et al, 1984).

In regard to local stimulation of estrogen receptor availability by melatonin in cutaneous areas of androgenic and estrogenic hormone sensitivity. There is evidence that melatonin increases cytoplasmic estrogen receptor activity in hamster uteri and similar effects have been observed in estrogen receptor binding activity in human breast cancer cells (Danforth et al., 1983).

Other reviews of the physiological role of melatonin are found in:

G. M. VAUGHN et al., titled "Evidence for a pineal-gonal relationship in the human", published in Prog. Reprod. Biol Vol. 4, pp. 191–223, 1978.

H. L. JUDD, titled "Biorhythms of gonadotrophins and testicular hormone secretion", published in Endocrine Rhythms, 1979.

D. P. CARDINALI et al, titled "Melatonin action: sites and possible mechanisms in brain", published in "The pineal gland and its endocrine role", J. AXELROD, F. FRASCHINI and G. P. VELO, eds. Proc. Nato Adv. Study, Erice, Italy, pp. 551–575, Plenum Press, New York, 1982.

R. J. WURTMAN, et al., titled "The secretion and effects of melatonin in humans", published in "The pineal gland and its endocrine role", J. AXELROD, R. FRASCHINI and G. P. VELO, ed. Proc. nato Avd., Erice, Italy, pp. 551–575, Plenum Press, New York, 1982.

The Third Colloquim of the European Pineal Study Group, PECS 1984, published in EPSG Newsletter of August, 1984.

R. J. Wurtman et al, entitled "Physiological Control of Melatonin Synthesis and Secretion: Mechanism Generating Rhythms in Melatonin, Methoxytryptophol, and Arginine Vasotocin Levels and Effects on the Pineal of Endogenous Catecholamines, The Estrous Cycle, and Environmental Lighting", J. of Neural Transmission, Suppl. 13, 59–70 (1978).

Ivor Smith, entitled "Indoles of Pineal Origin: Biochemical and Physiological Status", Psychoneuroendocrinology, Vol. 8, No. 1, pp. 41–60 (1983).

Surprisingly, none of the prior art studies are concerned with the dermatological effects of the administration of melatonin to a human host. Moreover, there have been no previous studies regarding the topical application of melatonin, its homologues or derivatives for humans. The prior art studies do indicate that the compounds of the invention can be safely administered to humans in the treatment of various diseases.

SUMMARY OF THE INVENTION

In accordance with the present invention, there is provided a method and composition for treating the skin and scalp of a mammal by the administration of a composition containing a melatonin compound in order to improve the cosmetic, physical appearance or functional role.

More particularly, the present invention provides a composition for use in the treatment of skin and/or scalp of a human host in order to enhance the skin's condition and tone, prevent or ameliorate the conditions or symptoms of acne, seborrhea, hirsuitism and for the rejuvenation of live but degenerated hair follicles.

The preferred active of the compositions of the invention consists of melatonin itself. Among the chemical homologues useful for the production of compositions according to the invention, there can be mentioned the class of compounds which are represented by the general formula:

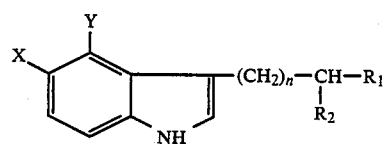

in which:

n is 1 or 2

$R_1$ and $R_2$ are identical or different from each other and are H, $NH_2$, COOH, OH or N-acyl comprising from 1–4 carbon atoms or alkoxy comprising from 1 to 4 carbon atoms:

X is OH or alkoxy comprising from 1–4 carbon atoms:

Y is H, OH or $NH_2$.

Preferred compounds for use in the compositions of the invention are those in which Y is hydrogen and X is methoxy. The most preferred compound is melatonin itself, the formula of which is:

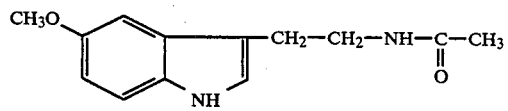

Other preferred compounds for use in the compositions of the invention are 5-methoxytryptamine, 5-methoxytryptophan, 5-methoxytryptophol, 5-methoxyindole-3-acetic acid and 6-hydroxy-melatonin.

These compounds can be obtained by synthetic processes, general methods of manufacture which can be derived from those published by J. SZMUSZKOVICZ "Synthesis of N-acetyl-5-methoxy-tryptamine", J. Org. Chem. 25, 857 (1960), J. SUPNIEWSKI et al., "Synthesis of melatonin (5-methoxy-N-acetyltryptamine", published in Bull. Acad. Polon. Sci. Ser. Biol., 8, pp 479–481, 1960; or MASHKOVSKY et al. in Farmakol. Toksikol., 26, n 1, 10, 1963, said methods being of course in each case adapted to the particular compound sought.

The term "melatonin" is used hereafter to designate both the actual melatonin and the chemical homologues or derivatives thereof.

DESCRIPTION OF THE PREFERRED EMBODIMENTS

In a first preferred embodiment of the invention, the composition is in a form suitable for topical application for humans. Advantageously, this composition is in the form of a cream, ointment or lotion or another cosmetic liquid applicable externally. Such composition is then of a particular utility for preventing, attenuating or curing acne or for conditioning the skin to improve its appearance and texture.

Acne is a common inflammatory pilosebaceous disease characterized by comedones, papules, pustules, inflamed nodules, superficial pus-filled cysts, and, in extreme cases, canalizing and deep inflammed, sometimes purulent sacs. Its pathogenesis is complex; an interaction between hormones, keratinization, sebum and bacteria somehow determines the course and severity of the disease. The common form of acne is a feature of adolescence in both sexes, and androgen seems to be the essential factor, operating through stimulation of the sebaceous glands. Acne lesions predominate on the face but are also common on the neck, chest, upper back and shoulders.

The compositions in accordance with the present invention are particularly useful in the management of simple uncomplicated acne, such as, acne vulgaris. Acne vulgaris is a condition which involves the eruption of papules and pustules on an inflammatory base. The condition occurs primarily during puberty and adolescence due to overactive sebaceous apparatus which is believed to be affected by hormonal activity.

The other components of such compositions can be the usual ones. It is advantageous to use compositions in which melatonin is associated with a lipophylic substance, both being dissolved in an appropriate solvent. For instance, the melatonin homologues may be used in the form of a solution in a water-ethanol mixture containing from 10% to 30% v/v or more of ethanol. However, the amount of active ingredients may be more or less depending on the specific conditions to be treated and the degree of treatment needed.

The compositions for acne and seborrhea control or skin conditioning can also be used in a therapeutic environment or application, in addition to the cosmetic uses which have been mentioned here above. Particularly, the composition of the invention, whether it be used locally or regionally in the form of a cream, ointment or lotion or of another form of composition, can also be used for the prevention or treatment of androgen or drug-induced acne or seborrhea, for instance, in patients subjected to androgenous hormone therapy in cancer therapy.

In addition, melatonin can be used alone or in conjunction with topical estrogens to enhance topical or endogenous estrogen action on the skin for the prevention and treatment of acne or seborrhea or for cosmetic effects related to improving the texture and physical appearance of aging skin.

The prime use of melatonin, alongor in conjunction with estrogens will be during adolescence when the oiliness of skin and the plugging of sebaceous glands results in acne vulgaris and seborrhea. Alternatively, alone or in conjunction with estrogen in pre or post menopausal women where dryness and loss of skin texture has been ascribed to the decline in estrogen. The estrogens may be applied separately or in combination with the melatonin.

An additional use of melatonin is by direct application to the vaginal mucosa, aloneor in conjunction with estrogen to restore the quality and secreting capacity of atrophic sexual skin in the vagina.

The topical application of melatonin, alone or in conjunction with estrogen (oral or parenteral administration) will improve the texture (elasticity and vascularity) of skin subject to atrophy seen in association with the loss of estrogen with aging.

Whatever the use of the topical composition or lotion, the concentration of the active compound therein should be sufficient for providing a good local absorption of the active ingredients.

The mechanism of melatonins local action is based on the observations that it causes a local increase of the binding activity of estrogen receptors and can ameliorate the action of testosterone on the skin through enhancement of the local effect of estrogen.

In regard to the above, the cause of acne vulgaris and seborrhea (increased sebum production, oily skin) can be due to an excess of testosterone or related androgenic hormones. Current treatment of acne vulgaris includes the topical or systemic use of agents that provide estrogen or suppress the production of testosterone.

A suitable acne preparation may comprise the following;

Melatonin 10% in a colorless, greaseless lotion which contains water, aluminum hydroxide, isopropyl stearate, PEG-100 stearate, glyceryl stearate, cetyl alcohol, glycereth-26, isocetyl stearate, glycerin, dimethicone copolyol, sodium citrate, citric acid, methylparaben, propylparaben, fragrance. The preparation amongst the beneficial effects which the preparation provides are:

1. helps heal and prevent acne pimples. Melatonin dries up and kills acne causing bacteria to help prevent new ones.

2. helps absorb excess skin oil often associated with acne blemishes. The preparation preferably contains aluminum hydroxide, or other like materials, such as bentonite, which is a special oil absorbing ingredient that allows the lotion to absorb more excess skin oil than melatonin alone.

3. helps the skin look fresh. Extra oil absorption helps the skin look less oily, more natural. If desired, the preparation can also contain sulfur and/or recorcinol or other known active ingredients to help heal the acne pimples. However, the additional ingredients may be applied separately.

The following publications which are incorporated herein by reference describe the various methods of treating the acne condition:

C. R. DARLEY et al., titled: "Circulating testosterone, sex hormone binding globulin and prolactin in women with late onset or persistent acne vulgaris". Br. J. Dermatology, 106: 517–522

G. S. GINSBERG et al. (1981) titled: "Androgen abnormalities in acne vulgaris". Acta Dermatovener 61: 431–434.

R. PALATSI, et al., (1978) titled: "Treatment of acne with cyproterone acetate and ethenyl estradiol". Acth Dermatovener 58: 449–454.

J. H. CHERK (1980) titled: "Improvement of intractable acne in man following testosterone suppression using danazol". Cutis: 26: 393–394.

J. B. SCHMIDT, J. SPONA (1983) titled: "Hormone recpetors in normal skin and acne". Endocrinologica Experimentalis 17: 137-144, 1983.

J. ZABEL: titled: "Uptake of $^3$H-testosterone in the skin of healthy women and in the skin of patients with acne vulgaris". Acth Histochem: 64: 243-248.

As previously mentioned, melatonin has been shown to have a direct effect on the metabolism of steroids in peripheral organs such as ovary, testes, adrenals and prostate. Thus, its action on the skin may be by cutaneous alteration in the metabolism of androgens, i.e., blocking the targeting effects of testosterone on sebaceous glands and hair follicles. Alternatively, melatonin may produce its therapeutic effect via an increase in estrogenic receptors in the skin and seborrheic glands. Melatonin can feminize the skin by increasing its capacity to respond to estrogen through an increase in cutaneous estrogen receptors or through an attenuation of androgen response.

The action of estrogen as a skin conditioner is enhanced by melatonin's local action in modulating the increase in estrogenic receptors. Thus melatonin's action on aging skin of postmenapausal women or aging males is mediated by enhancing local estrogenic effects. This is of value in restoring cosmetic quality to the skin (moisture, vascularity, elasticity) as well as restoring the local response of vaginal epithelium to estrogen.

More generally, the compositions of the invention (either in the form of lotions, creams, or ointments) of the invention are useful for the up-keeping of skin in good condition or for skin-regeneration, particularly in an aging population. The administration or use of melatonin will allow in particular the restoration of the skin functions including elasticity and moisture content. Even more generally melatonin is capable of controlling body odors by altering sebaceous secretions, the up-keeping of skin moisture and of all key factors associated with hormones involved with hair growth which govern in part sexual attraction. The invention particularly includes perfume compositions deodorants or toiletries supplemented with melatonin.

A second preferred embodiment of the invention relates to compositions containing melatonin, their chemical homologues and derivatives, for preventing hair growth in androgenic skin sensitive areas that are cosmetically of concern for aesthetic and sexual differentiation reasons, i.e., face, upper lip, chin, cheeks, neck or on the body: check, breast, nipples, abdomen, pelvic triangle, shoulders, back, buttock and extremities.

This particular invention provides selective regionalized or local hair loss, hair prevention, slowing or attenuation of hair growth in areas of androgenic (masculine) growth patterns where hirsuitism is considered superfluous.

This embodiment of the invention involves the application of melatonin, its homologues or derivatives for the control of:

(1) Facial Hair: To decrease the frequency or eliminate the need for shaving or to make the beard more amenable to shaving.

(2) Hirsuitism: Hirsuitism is defined as excessive hair growth in areas usually not hairy. In most instances, excessive growth of body hair in women cannot be traced to an endocrine cause, but occasionally a mild androgenic influence of ovarian or adrenal origin is suspect. Hirsuitism is seen frequently at menopause and with systemic androgenic steroid or corticosteroid therapy, and may occur in porphyia cutanea tarda. To reverse or prevent excess terminal hair growth in areas of excess (androgenic) masculine growth patterns. This is particularly applicable to women to control facial or body hair to meet cultural or individual views of what is cosmetically acceptable regarding facial or body hair. Hirsuitism is a problem in as many as 5% of women or even more depending on esthetic or cultural values.

This invention strictly considered should not be considered to be a depilatory but in effect a modulator and attenuating influence on the stimulating action of androgenic hormones on hair growth. In this regard, androgenic hormones are responsible for facial hair growth in men and women as well as the male pattern of body hair and the thickness and quantitative measurement of hair growth as part of a spectrum of virilization of which hirsuitism can be a significant part.

The following publication which is incorporated herein by reference discloses additional methods of treating hirsuitism which may be used in conjunction with the present invention.

HATCH et al. titled "Hirsuitism: implications, etiology and management" Am. J. Obstetrics and gynecology 140: 815-830, 1981.

In regard to the application of melatonin for the control of facial and body hair, it is advantageous to use compositions in which melatonin is associated with a lipophilic substance, both being dissolved in an appropriate solvent. For instance, the melatonin homologues are used in the form of a solution in a water-ethanol mixture containing from 10% to 30% v/v or more of ethanol. Alternatively, it can be administered as a cream or ointment. However, the amount of active ingredients in the composition may be more or less depending on the specific conditions to be treated and the degree of treatment needed.

The compositions for hair control can also be used in a therapeutic environment or application, in addition to the cosmetic uses which have been mentioned here above. Particularly, the composition of the invention, whether it be in the form of a lotion or of another form of composition, can also be used for the prevention or treatment of hormone-induced virilization, for instance in patients subjected to androgen hormone therapy in cancer therapy or with corticosteroid administration for anti-tumor or anti-inflammatory action which, as it is well known, can cause temporary or prolonged hirsuitism. The topical application of melatonin can avoid or attenuate hormone induced hirsuitism.

Alternative medical uses for melatonin are seen in its application to prevent or attenuate hair growth wherein frequent shaving results in significant irritation.

To avoid furunculitis or ingrown hairs and to ease the discomfort of adhesive bandage removal and depilation for cosmetic purposes.

Whatever the use of the topical composition or lotion for attenuating or preventing hair growth, the concentration of the active compound therein should be sufficient for providing a good local absorption of the active principle. It is believed that melatonin, when so applied, causes a local increase of the binding activity of estrogen receptors and also neutralizes the action of local testosterone.

The compositions can also be in a form suitable for oral administration in combination with topical treatment. These oral compositions then containing an effective amount of the active compound to produce the same effects. The complete innocuity and absence of toxic side effects of melatonin are well known.

By way of example, relative concentrations of $10^{-4}$ percent to above 1 percent in weight of the melatonin or melatonin derivatives in lotions or other liquid solutions of $10^{-4}$ percent to 1 percent in ointment or cream compositions. When oral use is considered, effective daily dosages range from about 0.1 to about 100 mg/kg/day, the solid orally administrable compositions being dosed accordingly.

The different fields of application which have been mentioned above should not be considered as limitative. It goes without saying that the invention is applicable to any field involving limitation of hair growth in androgenically responding cutaneous sites.

A third embodiment of the invention relates to compositions containing an effective amount of melatonin associated with a vehicle which makes said composition suitable for topical application for preventing hair fall or regeneration of hair to the extent where the hair roots or follicles are not yet fully degenerated or dead. That is, hair follicles which are still capable of sustaining hair growth and can be rejuvenated. As a matter of fact, it has been found that the definitive death of hair often takes place about 3 or 4 years after the actual fall. Therefore, under such circumstances, renewed growth of hair which is not yet dead can even be observed. The other components of such compositions can be the usual ones. It is advantageous to use compositions in which melatonin is associated with a lipophylic substance, both being dissolved in an appropriate solvent. For instance, the melatonin homologues are used in the form of a solution in a water-ethanol mixture containing from 10% to 30% v/v or more of ethanol. However, the amount of active ingredients in the composition can be more or less depending upon the patient, the conditions of the scalp and the effect desired.

In accordance with the present invention, the compositions for hair control or regeneration can also be used in therapeutical environment or application, in addition to the cosmetic uses which have been mentioned here above. Particularly, the composition of the invention, whether it be in the form of a lotion or of another form of composition, can also be used for the prevention or treatment of drug-induced or toxic alopecia, for instance in patients subjected to androgenous hormone therapy or cancer chemotherapy which, as it is well known, often causes temporary complete hair fall. The topical application of melatonin then both slows down the drug-induced alopecia, and/or favors the hair recovery when the therapy concerned is over.

Toxic alopecia is distinguishable from male-pattern baldness. Toxic alopecia is usually temporary and may follow a severe, often febrile illness. It may also be seen in myxedema, hypopituitarism, following pregnancy, and with some drugs. In such cases there is degeneration of the hair follicles which unless stimulated or rejuvenated would result in a permanent loss of the hair follicles.

Whatever the use of the topical composition or lotion, the concentration of the active compound therein should be sufficient for providing a good local absorption of the active principle. It is believed that melatonin, when so applied, causes a local increase of the binding activity of estrogen receptors and also neutralizes the local testosterone.

The topical application in a significant number of persons who use a melatonin lotion by topical head application, resulted in the complete interruption of the hair fall which they were experiencing previously. Melatonin was also found to act in them as a regulator of sebaceous glands.

Prior to the present invention, there have been no clinical or laboratory studies with regard to the topical application of melatonin to cutaneous areas.

The following tests were conducted utilizing ten male subjects suffering from hair loss and baldness, a preparation containing melatonin in a concentration of 1 mg/ml in 30% ethyl alcohol.

The solution of melatonin (Fluka AG, Buchs, Switzerland) was prepared containing 1 mg/ml in 30% ethyl alcohol. The solution was kept in a dark bottle at 4 degrees C. The stability of melatonin in the solution was periodically checked by HPLC and no degradation or changes were observed in the course of three months.

A group of ten balding men with variable degree of hair loss, dander and sebaceous, fatty secretion of the scalp, aging 30 to 50 years, were treated daily in the evening (6 to 10 p.m.) with topic applications of melatonin by imbibition of the balding areas with melatonin solution combined with a light massage of the scalp for five minutes. The solution was left to dry and to act overnight. The treatment was continued for two weeks and then continued at three day intervals, twice a week for a further three months.

The effect of melatonin on scalp hair was evident after a few days of initiation of its topical application. Loss of hair first decreased and then completely stopped and permanently abrogated. Thinning, brittle fragile hair in balding areas grew vigorously and became identical to healthy normal hair in those areas maintaining hair growth. However, completely bald areas where hair had been lost for a long time (years), did not show any regeneration of hair growth. Also, in the areas treated with melatonin, dander, epitherlial desquamation and excessive sebaceous secretion disappeared completely and the scalp skin showed a clean, healthy, elastic appearance. Apparently, hair pigmentation was not affected. While, greying hair or black hair maintained their original color. When the treatment was interrupted for two weeks, a modest hair loss was observed which was immediately reversed by further continuation of melatonin application. No significant or alarming local or general toxic side effects of topic administration of melatonin have been observed at five months after beginning of the tests.

Even when administered per os at very high doses and for a long time, melatonin has been found to be singularly free of toxicity. Thus, topic use of melatonin does not constitute a danger if one considers that, in humans, pineal secretion of melatonin is a normal physiologic event with typical night-day periodicity.

This activity of melatonin on restoration and maintenance of scalp hair growth does thus constitute a valid "physiological" prophylaxis and therapy of the balding syndrome in humans suffering from toxic alopecia.

Although the invention relates primarily to the topical application of melantonin, it is understood that topical treatment may be in combination with oral or parenteral administration of melantonin depending upon the patient and the severity of the condition to be treated.

By way of example, there may be mentioned merely by way of examples, relative concentrations of $10^{-4}$ percent to about 1 percent in weight, of the melatonin or melatonin derivatives in lotions or other liquid solutions of, $10^{-4}$ percent to 1 percent in ointment compositions. Other suitable pharmaceutical carriers which may be utilized in the invention are described in F. W. Martin et al. "Remington's Pharmaceutical Sciences" 14th Ed. Mack Publishing Company, Easton, Pa. 1965, which is incorporated herein by reference.

Generally, it is advantageous to apply or use the compositions of the invention in the evening and prior to going to slep when melatonin endogenous production is reduces at a lower level. However, this is not a limiting condition for the use of melatonin compositions.

The following references together with other references which are mentioned hereinbefore relate to studies on various animal in the treatment of various conditions and are herein incorporated by reference.

REFERENCES (1) Flaugh, M. E., Crowell, T. A., Clemens, J. A., Sawyer, B. D.: Synthesis and evaluation of anti-ovulatory activity of a variety of melatonin analogues. J. Med. Chem. 22: 63–69, 1979.

(2) Frohn, M. A., Seaborn, C. J., Johnson, D. W., Phillipou, G., Seamark, R. F., Matthews, G. D.: Structure-activity relationship of melatonin analogues. Life Sciences 27: 2043–2046, 1980.

(3) Kelly, R. W., Amato, F., Seamark, R. F.: N-Acetyl-5-merthoxy kynurenamine, a brain metabolite of melatonin, is a potent inhibitor of prostaglandin biosynthesis. Biochem. Biophy. Res. Commun. 121: 372–379, 1984.

(4) Marangos, P. J., Patel, J., Hirata, F., Sonheim, D., Paul, S. M., Skolnick, P., Goodwin, F. K.; Inhibition of diazepam binding by tryptophan derivatives including melatonin and its brain metabolite N-acetyl-5-methoxy kynurenamine. Life Sciences 29: 259–267, 1981.

(5) Pevet, P.: Is 5-methoxytryptamine a pineal hormone? Neuroendocrinology 8: 61–73, 1983.

(6) Richardson, B. A., Vaughn, M. K., Petterborg, L. J., Johnson, L. Y., King, T-S., Smith, I., Reiter, R. J.: Natural and synthetic analogues of melatonin and related compounds. Effects on the reproductive system of the male syrian hamster. J. Neurol. Transmission 56: 187–197, 1983.

(7) Rollag, M. D.: Ability of tryptophan derivatives to mimic melatonin's action upon the syrian hamster reproductive system. Life Sciences 31: 2699–2707, 1982.

(8) Vaughan, M. K., Richardson, B. A., Johnson, L. Y., Petterborg, L. J., Powanda, M-C., Reiter, R. J., Smith, I.: Natural and synthetic analogues of melatonin and related compounds. II Effects on plasma thyroid hormones and cholesterol levels in male syrian hamsters. J. Neural Trans. 56: 279–291, 1983.

(9) Anton-Tay, F., Diaz, J.L., Fernandez-Guardiola: On the effect on melatonin upon human brain: Its possible therapeutic implications. Life Sciences 10: 841–850, 1971.

(10) Anton-Tay, F.: Melatonin: Effects on brain function. Advance Biochem Psychopharmacol. 11: 315–324, Raven Press, N.Y., 1974

(11) Arendt, J., Symons, A. M., Laud, C. A., Pryde, S. J.: Melatonin can induce early onset of the breeding season in ewes. J. Endocrinol 97: 395–400, 1983.

(12) Arendt, J., Borbely, A. A., Franey, C., Wright, J.: The effects of chronic, small doses of melatonin given in the late afternoon on fatigue in man: A preliminary study. Neuroscience Letters 45: 317–321, 1984.

(13) Bartness, T. J., Wade, G. N.: Photoperiod control of body weight and energy metabolism in Syrian hamsters (mesocricetus auratus) role of pineal gland, melatonin, gonads and diet. Endocrinology 114: 492–498, 1984.

(14) Bittman, E. L.: Melatonin and photoperiodic time measurement measurement: Evidence from rodents and ruminants. The Pineal Gland, ed. R. J. Reite, Raven Press, N.Y., pp. 155–192, 1984.

(15) Blask, D. E.: The pineal, and oncostatic gland? In: The Pineal Gland. ed. R. J. Reiter, Raven Press, New York, 1984, pp. 276–277.

(16) Bubenik, G. J.: Shift of seasonal cycle in white-tail deer by oral administration of melatonin. J. Exp. Zool. 225: 155–156, 1983.

(17) Burns, J. K.: Administration of melatonin to non-human primates and to women with breast carcinoma. J. Physiol. 229: 38–39, 1973.

(18) Carman, J. S., Post, R. M., Buswell, R., Goodwin, F. K.: Negative effects of melatonin on depression. Amer. J. Psychiatr. 133: 1181–1186, 1976.

(19) Cotzias, G. C., Papavasiliou, P. S., Ginos, J., Steck, A., Duby, S.: Metabolic modification of Parkinson's disease and of chronic manganese poisoning. In: Ann. Review of Medicine, ed. A. C. Degraff, W. P. Cregor. 22: 305–326. Ann Revs Inc., Palo Alto, 1971.

(20) Cramer, H., Rudolph, J., Consbruch, U., Kendel, K.: On the effects of melatonin on sleep and behavior in man. Adv. Biochem. Psychopharmacol. 11: 187–191, Raven Press, New York, 1974.

(21) Danforth, J. R., Tamarkin, L., Do, R., Lippman, E.: Melatonin induced increase in cytoplasmic estrogen receptor activity in hamster uteri. Endocrinology 113: 81–85, 1983.

(22) Danforth, D. N., Jr., Tamarkin, L., Lippman, M. E.: Melatonin increases estrogen receptor binding activity of human breast cancer cells. Nature 305: 323–325, 1983.

(23) Ellis, L. C.: Inhibition of rat testicular androgen synthesis in vitro by melatonin and serotonin. Endocrinology 90: 17–28, 1972.

(24) Ellis, L. C., Urry, R. L.: Direct in vitro effects of melatonin on steroid biotransformation. Physiologist 15: 125, 1972.

(25) Fiske, V. M., Parker, K. L., Ulmer, R. A., Hoonow, H., Aziz, N.: Effect of melatonin alone or in combination with human chorionic gonadotropin or ovine luteinizing hormone on the in vitro secretion of estrogens on prosterone by granulosa cells of rats. Endocrinology 114,: 407–410, 1984.

(26) Frehn, J. L., Urry, R. L., Ellis, L. C.: Effect of melatonin and short photoperiod on delta-4-reductase activity in liver and hypothalamus of the hamster and the rate. J. Endocrinol. 60: 507–515, 1974

(27) Heath, H. W., Lynch, G. R.: Intraspecific differences for melatonin-induced reproductive regression and the seasonal molt in peromyscus leucopus. Gen and Comp. endocrinol. 48: 289–295, 1982.

(28) Horst, H-J, Buck, A., Adam, K-U: Orally administered melatonin stimulates the 3 alpha/beta hydroxy steroid oxidoreductase but not the 5 alpha reductase in the ventral prostate and seminal vesticles of pinealectomized rats. Experientia 38: 968–970, 1982.

(29) Houssay, A. B., Pazo, J. H., Epper, C. E.: Effects of the pineal gland upon the hair cycles in mice. ACTA Physiol. Lat. Am. 202–205, 1966.

(30) Houssay, A. B., Pazo, J. H., Epper, C. E.: Effects of the pineal gland upon the hair cycles in mice. J. Invest. Dermatol. 47: 230–234, 1966.

(31) Kennaway, D. J., Seamark, R. F.: Circulating levels of melatonin following its oral administration or subcutaneous injection in sheep and goats. Aust. J. Biol. Sci. 33: 349–53, 1980.

(32) Kennaway, D. J., Gilmore, T. A., Beamark, R. F.: Effect of melatonin feeding on serum prolactin and gonadotropin levels and the onset of seasonal estrous cyclicity in sheep. Endocrinology 110: 1766–1772, 1982.

(33) Kennaway, D. J., Gilmore, T. A.: Effect of melatonin implants in ewe lambs. J. Reprod. Fert. 70: 39–45, 1984.

(34) Lerner, A. B., Norlund, J. J.: Melatonin: Clinical Pharmacology J. Neural Transm. (Suppl.) 13: 339–347, 1978.

(35) Lincoln, G.: Melatonin as a seasonal time cue: The commercial story. Nature 302: 755, 1983.

(36) Losee, S. H. Turek, F. W.: Melatonin treatment prevents the termination of the gonadal refractory condition normally observed in hamsters exposed to long days. In *Pineal Function.* ed. C. D. Matthews, R. F. Seamark. Elservier/North Holland, pp. 67–75, 1981.

(37) Lovenberg, W.E., Jequier, E., Sjoerdsma, A.: Tryptophan hydroxylation: Measurement in pineal gland brainstem and carcinoid tumor. Science, 155: 217–219, 1967.

(38) Moeller, H., Koz, A., Rodl, W., Frick, H-J., Gupta, D.: Role of pineal gland in the regulation of prostatic androgen receptors in pubertal and mature rats. Res. Exp. Med. 183: 157–165, 1983.

(39) Nordlund, J. J., Lerner, A. B.: The effects of oral melatonin one skin color and the release of pituitary hormones. J. Clin. Endocrinol. Metabl 45: 768–774, 1977.

(40) Ogle, T. F., Kitay, J. I.: Effect of melatonin and an aqueous pineal extraction on adrenal secretion of reduced steroid metabolites in female rats. Neuroendocrinology 23: 113–120, 1977.

(41) Papavasiliou, P. S., Cotzias, G. C., Duby, S. E., Steck, A. J., Bell, M., Lawrence, W. H.: Melatonin and parkinsonism. JAMA 221: 88, 1972.

(42) Pavel, S., Goldstein, R., Petrescu, M., Popa, M.: Melatonin, vasotocin and REM sleep in prepuberal boys. Advanc. Biosciences 29: 343–347, 1981 in *Melatonin-Current Status and Perspectives,* ed. N. Birau, W. Schloot, Pergamon Press, NY, 1981.

(43) Peat, F., Kinson, G. A.: Testicular steroidogenesis in vitro in the rat in response to blinding, pinealectomy and to the addition of melatonin. Steroids 17: 251–264, 1971.

(44) Petterborg, L. J., Reiter, R. J.: Effect of photoperiod and subcutaneous melatonin implants on the reproductive status of adult white footed mice (percomycus leucopus) U. Androl. 2: 222–224, 1981.

(45) Pevet, P., Haldar-Misra, C., Ocal, T.: Effect of 5 methoxytryptaminme and 5 methoxytryptophol on the reproductive system of the male golden hamster. J. Neural Transmis. 51: 303–311, 1981.

(46) Pevet, P., Haldar-Misra, C.: Effect of orally administered melatonin on reproductive function of the golden hamster. Experientia 38: 1493–1494, 1982.

(47) Raikhlin, N. T., Kvetnoy, I. M. Tolkachev, V. N.: Melatonin may be synthesized in enterochromaffin cells. Nature 225: 344–345, 1975.

(48) Ralph, C. L.: Melatonin production by extra-pineal tissues. Adv. In the biosciences. ed.

(49) Rollag, M. D., Morgan, R. J., Niswender, G. D.: Route of melatonin secretion in sheep. Biomed. Sci. Instrum. 13: 111–117, 1977.

(50) Romijn, H. J.: The pineal, a tranquillizing organ? Life Sciences 23: 2257–2274, 1978.

(51) Rose, J., Stormshak, F., Oldfield, J., Adair, J.: Introduction of winter fur growth in mink (mustela vison) with melatonin. J. Animal Sci. 58: 57–61, 1984.

(52) Russel, J., Reiter: The pineal gland: An intermediary between the environment and the endocrine system. in Psychoneuroendocrinology 8: 31–40, 1983.

(53) Shirama, K., Furuya, T., Takeo, Y., Shimuzu, K., Maekawa, K.: Direct effect of melatonin on the accessory sexual organs in pinealectomized male rats kept in constant darkness. J. Endocrinology 95: 87–94, 1982.

(54) Sisk, C. L., Turek, F. W.: Daily melatonin injections mimic the short day-induced increase in negative feedback effects of testosterone on gonadotropin secretion in hamsters. Biol. of Reproduction 27: 602–608, 1982.

(55) Smythe, G. A., Lazarus, L.: Growth hormone response to melatonin in man. Science, 184: 1373–1374, 1974.

(56) Stetson, M. H., Rollag, M. D., Watson-Whitmyre, M, Tate-Ostroff, B.: The effect of daily injections and constant release implants of melatonin on the endogenous pineal rhythm in golden hamsters. Proc. Soc. Exp. Biol. Med. 174: 119–122, 1983.

(57) Stetson, M. H., Tay, D. E.: Time course of sensitivity of golden hamsters to melatonin injections throughout the day. Biol. of Reproduction 29: 432–438, 1983.

(58) Stetson, M. H., Watson-Whitmyre, M.: Physiology of the pineal and its hormone melatonin in animal reproduction in rodents. In: *The Pineal Gland,* ed. R. J. Reiter, Raven Press, New York, 1984, pp. 109–153.

(59) Tamarkin, L., Baird, C. J., Almeida, O. F. X.: Melatonin: A coordinating signal for mammalian reproduction. Science 227: 714–720, 1985.

(60) Trentini, G. P., Mess, B., DeGaetani, Poggioli, R., Ferrari, P., DiGregorio, C.: The role of melatonin and brain serotoninergic system in the maintenance of rat ovarian cyclicity. *Pineal Function,* ed. C. D. Matthews, R. F. Seamark. Elsevier/North-Holland, pp. 77–86, 1981.

(61) Turek, F. W.: Antigonadal effect of melatonin in pinealectomized and intact male hamsters. Proc. Soc. Exp. Biol. Med. 155: 31–34, 1977.

(62) Vaughn, M. K., Herbert, D. C., Brainard, G. C., Johnson, L. Y., Zeagler, J. W., Reiter, R. J.: A comparison of blinding and afternoon melatonin injections on the histology of the reproductive organs, pineal ultastructure and gonadotrophin hormone levels in female syrian hamsters. Adv. In the Biosciences. Ed. N. Birau, W. Schoot, V. 29: Melatonin-current status and perspectives. Pergamon Press, New York, 1981, pp. 65–75.

(63) Vollrath, L., Semm, P., Gammel, G.: Sleep induction by intranasal application of melatonin. Advanc. Biosciences 29: 327–329 *Melatonin-Current Status and Perspectives,* ed. N. Birau, W. Schloot, Pergamon Press, NY, 1981.

(64) Waldhauser, F., Lynch, H. J., Wurtman, R. J.: Melatonin in human body fluids: Clinical significance. *The Pineal Gland.* ed. R. J. Reiter. Raven Press, NY, p. 345–370, 1984.

(65) Wilson, B. W., Lynch, H. J., Ozaki, Y.: 5 methoxytryptophol in rat serum and pineal: detection, quantitation and evidence for daily rhymicity. Life Sci. 23: 1019–1024, 1978.

What is claimed is:

1. A method for conditioning the skin of a human host to improve its cosmetic and physical appearance which comprises topically administering to a site on the skin of said host an effective amount of a composition comprising a melatonin and a pharmaceutical carrier for causing improvement in the cosmetic and physical appearance of said skin.

2. The method of claim 1 wherein said melatonin enhances the local action of estrogen at the site administered.

3. The method of claim 1 wherein said melatonin attenuates the systemic action of androgens at the site administered.

4. A method for treating a patient afflicted with acne vulgaris or seborrhea which comprises topically administering to said patient to the site of said acne vulgaris or seborrhea an effective amount of a composition comprising melatonin and a suitable pharmaceutically acceptable carrier for causing a reduction of the symptoms or prevention of acne vulgaris or seborrhea development in said patient.

5. The method of claim 4 wherein said composition is applied to the face of said patient.

6. The method of claim 4 including administering a topical estrogen for enhancing endogenous estrogen action on the skin of said patient.

7. The method of claim 6 wherein said estrogen is administered in conjunction with said melatonin.

8. The method of claim 6 wherein said estrogen is administered separately from said melatonin.

9. The method of claim 4 wherein said acne vulgaris or seborrhea is androgenous hormone therapy induced.

10. A method for selectively decreasing body and facial hair growth by attenuating the stimulation of estrogen induced hair growth on a human host which comprises topically administering to said host an effective amount of a composition comprising melatonin and a pharmaceutically acceptable carrier for attenuating hair growth on said host.

11. The method of claim 10 wherein said composition is topically administered to the site on said host where attenuation of hair growth is required.

12. The method of claim 10 wherein said composition is administered to a site on said host wherein hair growth is by androgenous hormone therapy induced.

13. The method of claim 10 wherein said composition is administered to androgenically responding cutaneous sites of said host.

14. A method for the reduction of excessive hair fall of a human host where the hair follicles are not degenerated and can be made to grow, which comprises topically administering to said host a composition comprising an effective amount of melatonin and a suitable pharmaceutical carrier for causing reduction in the loss of said degenerated hair follicles.

15. The method of claim 14 wherein degeneration of said hair follicles treated is by androgenous hormone therapy induced.

16. The method of claim 14 wherein said melatonin causes a local increase of the binding activity of estrogen receptors and neutralizes the local testosterone.

17. The method of claim 14 wherein said composition is a solution containing said melatonin in a concentration ranging from $10^{-4}$ to 1 percent in weight.

18. A method for conditioning the skin of a human host to improve its cosmetic and physical appearance which comprises topically administering to a site on the skin of said host an effective amount of a composition comprising a compound selected from the group consisting of melatonin, 5-methoxytryptamine, 5-methoxytryptophan, 5-methoxytryptophol, 5-methoxyindole-3-acetic acid and 6-hydroxymelatonin and a pharmaceutical carrier for causing improvement in the cosmetic and physical appearance of said skin.

19. A method for treating a patient afflicted with acne vulgaris or seborrhea which comprises topically administering to said patient to the site of said acne vulgaris or seborrhea an effective amount of a composition comprising a suitable pharmaceutically acceptable carrier and a compound selected from the group consisting of melatonin, 5-methoxytryptamine, 5-methoxytryptophan, 5-methoxytryptophol, 5-methoxyindole-3-acetic acid and 6-hydroxymelatonin for causing a reduction of the symptoms or prevention of acne vulgaris or seborrhea development in said patient.

* * * * *